US009131950B2

(12) United States Patent
Matthew

(10) Patent No.: US 9,131,950 B2
(45) Date of Patent: Sep. 15, 2015

(54) LAPAROSCOPIC INSTRUMENT

(75) Inventor: Gudeman Matthew, Grayslake, IL (US)

(73) Assignee: ENDOPLUS, INC., Mundelein, IL (US)

( * ) Notice: Subject to any disclaimer, the term of this patent is extended or adjusted under 35 U.S.C. 154(b) by 666 days.

(21) Appl. No.: 13/447,169

(22) Filed: Apr. 14, 2012

(65) Prior Publication Data

US 2012/0265242 A1 Oct. 18, 2012

Related U.S. Application Data

(60) Provisional application No. 61/517,177, filed on Apr. 15, 2011.

(51) Int. Cl.
*A61B 17/00* (2006.01)
*A61B 17/29* (2006.01)
*A61B 19/00* (2006.01)

(52) U.S. Cl.
CPC .................. *A61B 17/29* (2013.01); *A61B 19/34* (2013.01); *A61B 2017/292* (2013.01); *A61B 2017/2946* (2013.01); *A61B 2019/4868* (2013.01)

(58) Field of Classification Search
CPC ............ A61B 2017/291; A61B 17/29; A61B 2017/292; A61B 19/34; A61B 2017/2946; A61B 2019/4868; A61B 17/2909; A61B 17/28; A61B 17/292
USPC ......... 606/205–209, 48, 51–52; 600/462, 464
See application file for complete search history.

(56) References Cited

U.S. PATENT DOCUMENTS

| | | | | |
|---|---|---|---|---|
| 5,174,300 A | * | 12/1992 | Bales et al. | 600/564 |
| 5,176,702 A | * | 1/1993 | Bales et al. | 606/208 |
| 5,290,308 A | * | 3/1994 | Knight et al. | 606/205 |
| 5,352,235 A | * | 10/1994 | Koros et al. | 606/174 |
| 5,368,606 A | * | 11/1994 | Marlow et al. | 606/170 |
| 5,489,290 A | * | 2/1996 | Furnish | 606/170 |
| 5,620,415 A | * | 4/1997 | Lucey et al. | 604/22 |
| 5,649,958 A | * | 7/1997 | Grimm et al. | 606/208 |
| 5,797,939 A | * | 8/1998 | Yoon | 606/167 |
| 5,810,879 A | * | 9/1998 | de Guillebon | 606/205 |
| 5,817,128 A | * | 10/1998 | Storz | 606/205 |
| 5,984,939 A | * | 11/1999 | Yoon | 606/170 |
| 6,001,096 A | * | 12/1999 | Bissinger et al. | 606/50 |
| 6,039,752 A | * | 3/2000 | Kimura et al. | 606/205 |
| 6,099,537 A | * | 8/2000 | Sugai et al. | 606/143 |
| 6,394,964 B1 | * | 5/2002 | Sievert et al. | 600/564 |
| 2002/0026202 A1 | * | 2/2002 | Honey et al. | 606/127 |
| 2002/0128682 A1 | * | 9/2002 | Prestel et al. | 606/205 |
| 2007/0112377 A1 | * | 5/2007 | Schneiter | 606/205 |
| 2008/0004656 A1 | * | 1/2008 | Livneh | 606/205 |
| 2011/0087268 A1 | * | 4/2011 | Livneh | 606/205 |
| 2012/0078292 A1 | * | 3/2012 | Banju | 606/206 |
| 2013/0345743 A1 | * | 12/2013 | Aue et al. | 606/205 |

* cited by examiner

*Primary Examiner* — Amy R Weisberg
(74) *Attorney, Agent, or Firm* — Justin Lampel

(57) ABSTRACT

The present device relates to a laparoscopic medical instrument, particularly those used for minimally invasive surgery. The instrument has a movable and a stationary handle portion and an extended shaft assembly with a removable actuating rod. An opening on the side of the stationary handle portion allows a user to visually confirm the removable actuating rod is locked into place within the movable handle portion. An opening in the back of the stationary handle portion allows for cleaning and visual inspection of the interior of the shaft assembly portion once the rod is removed. The actuating rod has a grasping mechanism for performing work during surgery. A flush port is located near the distal end of the stationary handle portion.

8 Claims, 4 Drawing Sheets

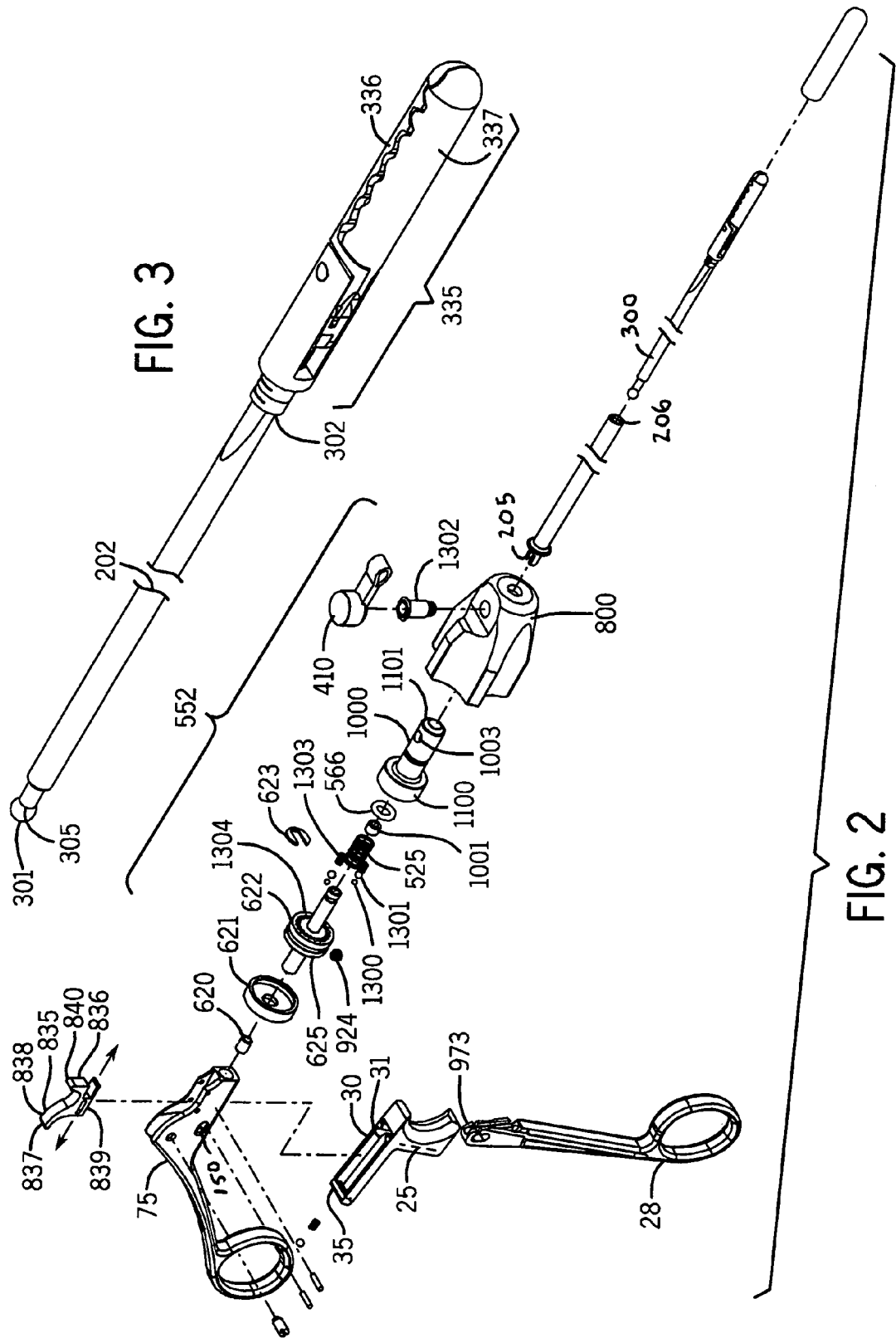

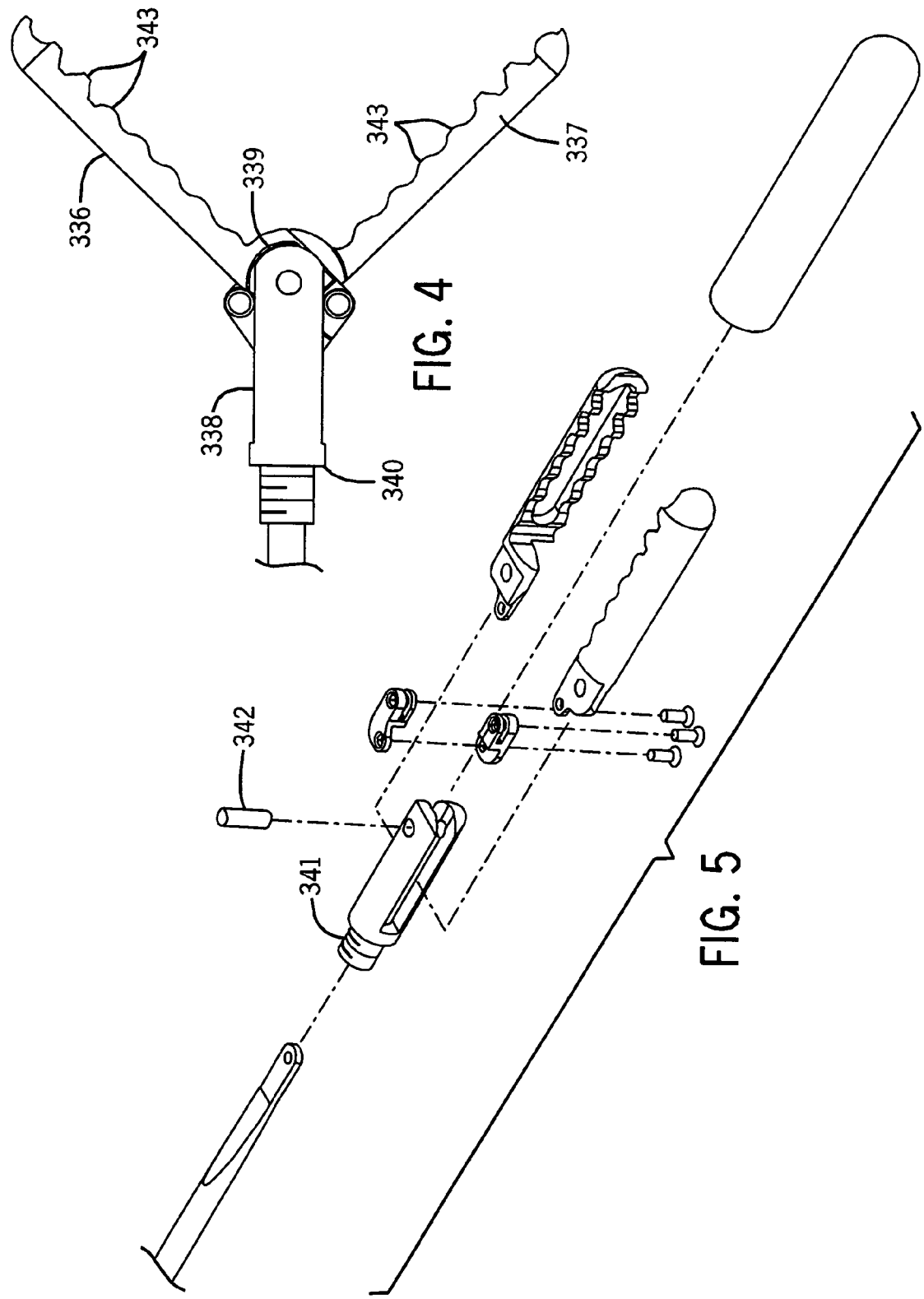

LAPAROSCOPIC INSTRUMENT

REFERENCE TO RELATED APPLICATIONS

The present application is based on U.S. provisional patent application No. 61/517,177 filed Apr. 15, 2011, the entire contents of which are incorporated by reference. Applicant claims the priority benefit of the 61/517,177 application.

BACKGROUND OF THE INVENTION

The present device relates to a laparoscopic medical instrument, particularly those used for minimally invasive surgery. The instrument has a movable and a stationary handle portion and an extended shaft assembly with a removable actuating rod. An opening on the side of the stationary handle portion allows a user to visually confirm the removable actuating rod is locked into place within the movable handle portion. An opening in the back of the stationary handle portion allows for cleaning and visual inspection of the interior of the shaft assembly portion once the rod is removed. When disassembled for the purpose of cleaning or for changing inserts, the handle assembly remains contained within itself to prevent handle components from being lost during reprocessing. The actuating rod has a grasping mechanism for performing work during surgery. A flush port is located near the distal end of the stationary handle portion.

Laparoscopic instruments have been used by surgeons during medical procedures since around 1900. There are many advantages of laparoscopic surgery compared with open procedure. These advantages include: reduced hemorrhaging which reduces needing a blood transfusion, smaller incision which reduces pain and shortens the recovery time of the patient, reduced scarring, reduced chances of needing pain medication, reduced hospital stays and quicker return to everyday life, and reduced risk of contamination and infection. Disadvantages of a laparoscopic procedure include: limited mobility of range of motion in the surgical site, poor depth perception by the surgeon, and often laparoscopic tools do not move in the same direction as the surgeons hands.

For example, U.S. Pat. No. 7,727,256 to McGregor discloses a surgical instrument having a shaft with a distal end portion and a proximal end portion; an operative device is disposed on the distal end portion. A hand mechanism has a first handle and a second handle and is disposed on the proximal end portion. Movement of the second handle relative to the first handle actuates the operative device. A ratchet, attached to the second handle, locks the operative device and moves with the second handle. The ratchet is pivotally attached to the second handle and pivots between a locked position and an unlocked position. A biasing device biases the ratchet toward the locked position and a release mechanism moves the ratchet from the locked position. At least one of the release mechanism and the ratchet has a feature permitting relative movement between the release mechanism and the ratchet.

U.S. Pat. No. 6,752,823 to Prestel discloses a surgical forceps having a jaw, with a handle consisting of two grip parts with which the one first grip part is connected to a forceps housing and the other second grip part is pivotable for opening and closing the jaw mouth, with an adjustment rod which is distally and proximally adjustable for opening and closing the jaw mouth and whose proximal end has a connection to a limb of the two limbed second grip part, and with at least one would spring element as an overload protection against the breakage of jaw parts. A particularly effective overload protection, a simple forceps construction and a small constructional size of the forceps are achieved according to the invention in that the spring element consists of a flat material wound in a serpentine manner with windings lying in one plane.

However, these patents fail to provide a laparoscopic instrument as defined in the present application. More specifically, these patents fail to define a laparoscopic instrument which has a flush port on a top end for cleaning, a locking mechanism on the handle, a viewing channel on the back end for visually verifying if the instrument is clean and for passing a brush through the interior lumen of the entire device for cleaning, a handle mechanism which is self contained, a keeper mechanism which both holds the self contained handle in a position which accommodates cleaning and sterilization and holds the self contained handle in a position which facilitates use during surgery, and an opening on the side for confirming a movable actuating rod is secured within the handle portion.

SUMMARY OF THE INVENTION

The present device relates to a laparoscopic medical instrument, particularly those used for minimally invasive surgery. The instrument has a movable and a stationary handle portion and an extended shaft assembly with a removable actuating rod. An opening on the side of the stationary handle portion allows a user to visually confirm the removable actuating rod is locked into place within the movable handle portion. An opening in the back of the stationary handle portion allows for cleaning and visual inspection of the interior of the barrel portion once the rod is removed. The actuating rod has a grasping mechanism for performing work during surgery. A flush port is located near the distal end of the stationary handle portion.

An advantage of the present laparoscopic instrument is that the device may be thoroughly cleaned and reused.

Yet another advantage of the present laparoscopic instrument is that a flush port may be located on a top side of the handle portion.

Still another advantage of the present laparoscopic instrument is that a user may visually inspect if any debris remains within the barrel of the device after the removable rod is removed from the barrel.

An advantage of the present laparoscopic instrument is that the device may be sterilized and reused.

Another advantage of the present laparoscopic instrument is that the movable handle portion may be locked into various positions during surgery.

And an advantage of the present laparoscopic instrument is that the user may visually confirm if the removable rod is secured properly within the handle portion.

Still another advantage of the present laparoscopic instrument is that the user may release the removable actuating rod easily.

And another advantage of the present laparoscopic instrument is that the instrument has a removable cap on the business end of the removable rod.

Still another advantage of the present laparoscopic instrument is that the handle assembly remains contained within itself when disassembled for the purpose of cleaning, sterilization, or changing inserts.

For a more complete understanding of the above listed features and advantages of the laparoscopic instrument, reference should be made to the following detailed description of the preferred embodiments and to the accompanying drawings.

BRIEF DESCRIPTION OF THE DRAWING

FIG. 2 illustrates an exploded view of the laparoscopic instrument.

FIG. 3 illustrates a perspective view of the grasping end of the laparoscopic instrument.

FIG. 4 illustrates a close up view of the grasping end of the laparoscopic instrument.

FIG. 5 illustrates an exploded view of the grasping end of the laparoscopic instrument.

DETAILED DESCRIPTION OF THE PREFERRED EMBODIMENTS

The present device relates to a laparoscopic medical instrument, particularly those used for minimally invasive surgery. The instrument has a movable and a stationary handle portion and an extended shaft assembly with a removable actuating rod. An opening on the side of the stationary handle portion allows a user to visually confirm the removable actuating rod is locked into place within the movable handle portion. An opening in the back of the stationary handle portion allows for cleaning and visual inspection of the interior of the barrel portion once the rod is removed. The actuating rod has a grasping mechanism for performing work during surgery. A flush port is located near the distal end of the stationary handle portion.

Figure 1:
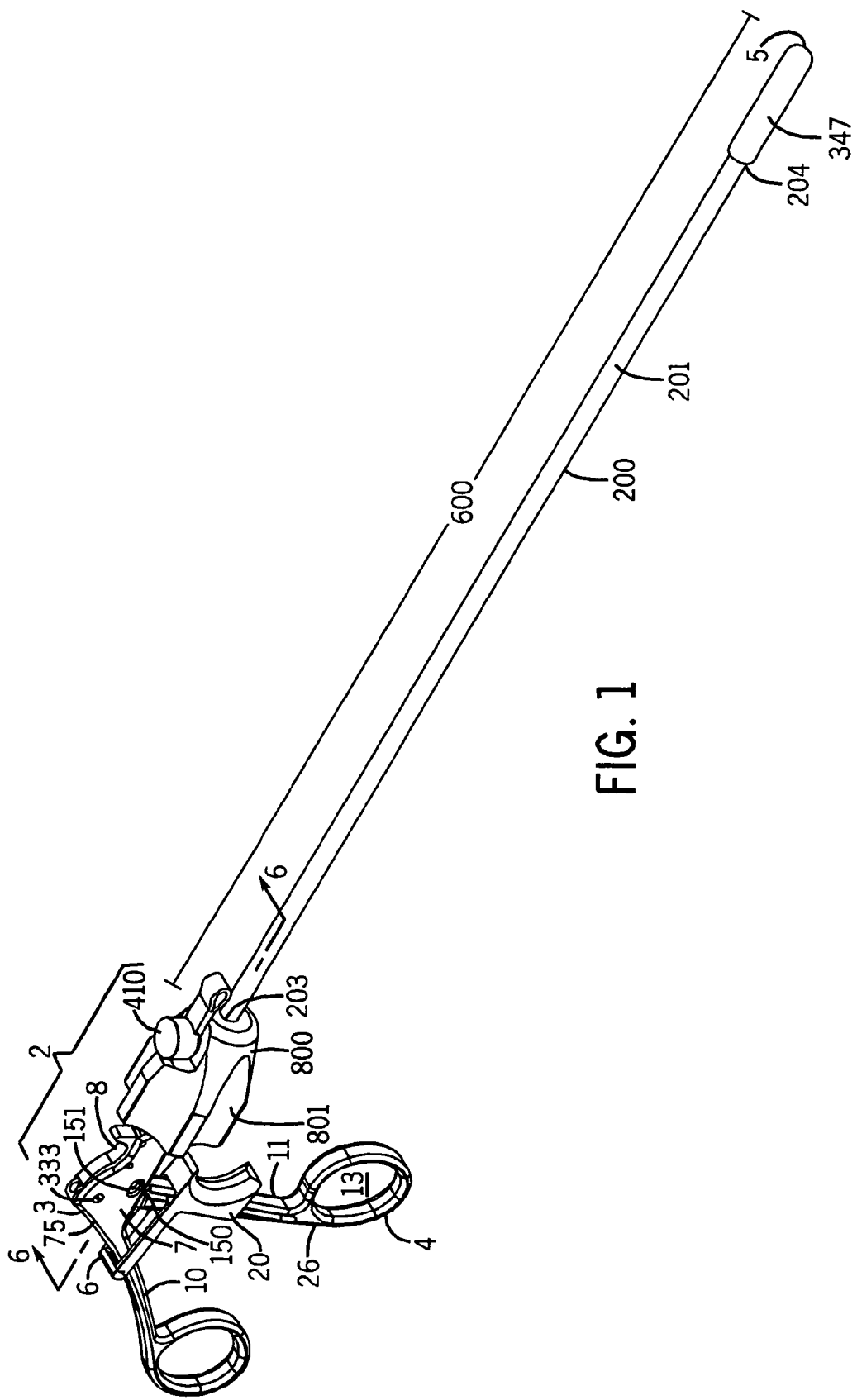
FIG. 1 illustrates a side perspective view of the laparoscopic instrument.

Referring now to FIG. 1, a laparoscopic instrument 1 is provided which is suitable for medical purposes. The laparoscopic instrument 1 may have a handle portion 2 and a shaft assembly portion 200 having a length 600. The laparoscopic instrument 1 may generally have a top 3, a bottom 4, a front 5, a back 6, a first side 7 and a second side 8. The laparoscopic instrument 1 may be constructed of various types of metal, plastics or the like.

The handle portion 2 of the laparoscopic instrument 1 may have a first end 33 and a second end 34. Further, the handle portion 2 of the laparoscopic instrument 1 may have a stationary member 10, a moveable member 11 and a handle portion housing 75. The top 973 (FIG. 2) of the movable member 11 may be visible on the top of the handle portion housing 75. The stationary member 10 may be directly connected to the handle portion housing 75 and further may be constructed as one unit. The stationary member 10 may remain stationary with respect to the handle portion housing 75 and the shaft assembly portion 200, while the movable member 11 may rotate with respect to the handle portion housing 75 and the shaft assembly portion 200. More specifically, the movable member 11 may rotate, for example, approximately forty-five degrees in a parallel manner with respect to the handle portion housing 75 and the shaft assembly portion 200.

The stationary member 10 and the movable member 11 may each have an opening 13 for receiving a finger of the surgeon. In an embodiment, the opening 13 of the stationary member 10 and the moveable member 11 may be of different sizes with respect to each other so as one may accommodate, for example, a thumb. Further, components of the device, including the opening 13 of the stationary member 10 and the moveable member 11, may vary in size and location depending on the intended function of the device 1 and may also vary depending on if the device 1 is intended for a right-handed person or left-handed person.

Figure 6:
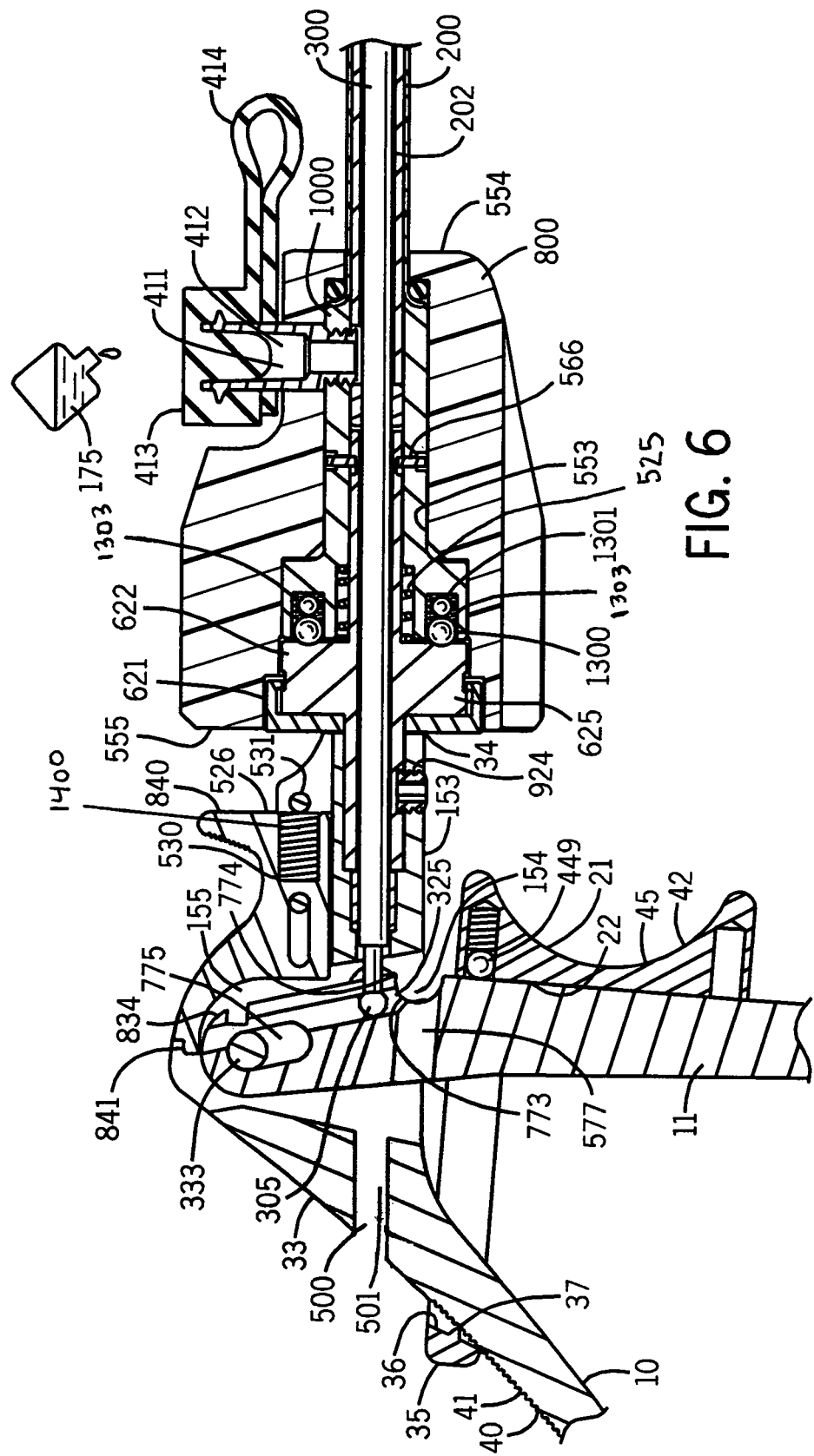
FIG. 6 illustrates a cross section of the laparoscopic instrument.

The handle portion housing 75 may have an interior 155 (FIG. 6). A pin 333 may be secured within the interior 155 of the handle portion housing 75. The pin 333 may act as a pivot point so as to allow the movement of the stationary member 10 with respect to the movable member 11. The pin 333 may extend from the first side 7 of the handle portion 2 to the second side 8 of the handle portion 2 and through the interior 155 of the handle portion housing 75. The pin 333 may run substantially perpendicular with respect to the shaft assembly portion 200 of the device 1.

The pin 333 may be located near the top 3 of the handle portion housing 75 of the laparoscopic instrument 1. As a result, the location of the pin 333 near the top 3 of the device may maximize the range of movement of the movable member 11 with respect to the stationary member 10. The pin also contains movable member 11 within stationary member 10 while allowing movable member 11 to move such that it can connect or disconnect from removable rod 300.

A rotation knob 800 may be connected to the shaft assembly portion 200. The rotation knob 800 may be generally cylindrical in shape and may have a first end 554 and a second end 555 wherein the first end 554 is located closer to the front 5 of the device 1 and the second end 555 is closer to the back 6 of the device 1. A series of large grooves 801 may surround the rotation knob 800 so as to provide the user with an optimal grasping surface. The rotation knob 800 may also have a port 410, as defined below. The rotation knob 800 may rotate three hundred and sixty degrees around an axis from the front 5 of the device to the back 6 of the device 1. Additionally, the rotation assembly is designed to lock when pressure is applied to the handles while putting a load on the jaws. This prevents the shaft assembly from turning until the load is removed from the jaws. The rotation assembly is designed to allow the shaft assembly to turn freely when there is no pressure applied to the handles resulting in a load on the jaws.

A screw 924 on the surface of the housing 75 may secure the shaft assembly 200 onto the handle. The shaft assembly portion 200 may therein be completely removed from the handle portion 2 for cleaning and or replacement.

A locking mechanism 20 may be secured around both the stationary member 10 and movable member 11. The locking mechanism 20 may have an exterior portion 21 and an interior portion 22. The interior portion 22 of the locking mechanism 20 may be obscured from view while the locking mechanism 20 is secured on the device 1. Within the interior portion 22 may be a ball bearing 449. The ball bearing 449 may allow the locking mechanism 20 to easily move vertically with respect to the movable member 11. Within the interior portion 22 of the locking mechanism 20 may be a vertical groove(s) 25. The vertical groove(s) 25 may run along a corresponding ridge 26 located on a front 28 of the movable member 11. The vertical groove(s) 25 and corresponding ridge 26 may run substantially the length of the movable member 11 of the handle portion 2.

The locking mechanism 20 may have a generally rectangular extension portion 30. The generally rectangular extension portion 30 may extend largely perpendicular with respect to the main body (and vertical groove 25) of the locking mechanism 20. The rectangular extension portion 30 may have a generally rectangular opening 31 defining a border having a back portion 35. The stationary member 10 and movable member 11 of the handle portion 2 may be partially located within, and may pass through, the generally rectangular opening 31 of the locking mechanism 20.

As stated above, the locking mechanism 20 may be moved vertically along the ridge 26 of the movable member 11. More specifically, the locking mechanism 20 may move up or down the movable member 11. The back portion 35 of the generally rectangular extension portion 30 may come into contact with the stationary member 10 wherein the stationary member 10 and movable member 11 are moved away from each other. The back portion 35 of the generally rectangular extension portion 30 may not contact the stationary member 10 when the moveable member 11 and the stationary member 10 are moved toward each other (while squeezing the device 1 to activate the jaw as defined below). The locking mechanism 20 is always in contact with the moveable member 11. As the locking mechanism 20 moves along the ridge 26 of the movable member 11 in a downward direction with respect to the top 3, the back portion 35 of the generally rectangular extension portion 30 may contact and stop the stationary member 10 and may reduce the angle for which the movable member 11 may move with respect to the stationary member 10. As a result, a surgeon may more accurately control the function of the device 1.

Referring now to FIG. 6, located on an interior surface 36 of the back portion 35 of the generally rectangular portion 30 may be ridge 37. Located along a back side 40 of the stationary member 10 may be a series of horizontal ridges 41. As the ridge 37 of the generally rectangular portion 30 contacts and interacts with the plurality of horizontal ridges 41, the locking mechanism 20 may be temporarily locked into place and desired movement of the movable member 11 may be restricted. To release the ridge 37 of the generally rectangular extension portion 30 from the series of horizontal ridges 41 the user may simply pull the locking mechanism 20 upward and away from the series of horizontal ridges 41. The front 42 of the locking mechanism 20 may have a curved portion 45 which may allow a user to easily manipulate the locking mechanism 20 on the movable member 11 of the device.

As stated above, the shaft assembly portion 200 of the laparoscopic instrument 1 may be generally cylindrical in nature and may extend away from the handle portion 2. In an embodiment, the shaft assembly portion 200 may have an exterior surface 201, an interior portion 202, a first end 203 and a second end 204. In an embodiment, an opening (not shown) may be located at the first end 203 and an opening 206 may be located at the second end 204 such that a fluid may pass through the interior portion 202 from the first end 203 to the second end 204 of the shaft assembly portion 200. While in use, the first end 203 of the shaft assembly portion 200 may be temporarily or permanently secured to a rotation assembly 552, which is in turn temporarily or permanently secured to the handle portion housing 75 of the device 1. Material coating on the outside of shaft assembly portion 200 of the laparoscopic instrument may have anti-microbial properties.

Referring now to FIG. 3, in an embodiment, located within the interior portion 202 of the shaft assembly portion 200 may be a removable rod 300 having a length. The length of the removable rod 300 may be greater than the length 600 of the shaft assembly portion 200 such that an end of the removable rod 300 extends beyond the first end 203 of the shaft assembly portion 200. The removable rod 300 may have a first end 301 and a second end 302. The first end 301 of the removable rod 300 may have a ball 305 which may be temporarily secured within a ball joint assembly socket 325 (FIG. 6) as defined below. The second end 302 of the rod 300 may be the business end of the rod 300 and may have, for example, a grasping mechanism 335 such as a movable jaw. A removable cap 347 (FIG. 1) may be placed over and may protect the grasping mechanism 335 while the device 1 is not being used.

The first side 7 and the second side 8 of the laparoscopic instrument 1 may have an opening 150 defining a hole. More specifically, the opening 150 may be located on the side of the handle portion housing 75 of the handle portion 2. The opening 150 may begin a channel 151 (within the interior 155 of the handle portion housing 75) extending from the first side 7 of the handle portion housing 75, through the interior 155 of the handle portion housing 75, to the second side 8 of the handle portion housing 75. As a result, a user may visually see through the channel 151 of the handle portion housing 75. An underside 153 of the handle portion housing 75 may also have an opening 154 located substantially below the channel 151 wherein a user may view a portion of the channel 151.

Located within the channel 151 of the handle portion housing 75 (and therein within the interior 155 of the handle portion housing 75) may be a movable ball joint assembly socket 325 for receiving the ball 305 of the removable rod 300. As a result of the opening 150, a user may visually inspect the device 1 to see if the ball 305 of the removable rod 300 is properly secured within the ball joint assembly socket 325 of the handle portion housing 75. Once the ball 305 is properly inserted within the ball joint assembly socket 325, the user may manipulate the movable member 11 to control the second end 302 (the business end) of the removable rod 300. A user may also inspect the ball 305 and ball joint assembly socket 325 from the opening 154 on the underside 153 of the device 1.

An opening 773 may be present near the top of the movable member 11 of the device 1. More specifically, the opening 773 may be physically an opening creating a cavity within the movable member 11. The opening 773 may form the ball joint assembly socket 325 (as described above) for receiving the ball 305 of the removable rod 300. A ridge 774 on the edge of the opening 773 may prevent the ball 305 from accidentally exiting the ball joint assembly socket 325.

The movable member 11 may have a generally oval opening 775 for receiving the pin 333. The generally oval opening 775 may be obscured from view within the interior 155 of the handle portion housing 75. The generally oval opening 775 may run largely parallel with respect to the movable member 11 such that the movable member 11 may slightly move up or down with respect to the stationary member 10. As a result, a user may move the movable member 11 up or down to remove the ball 305 from the ball assembly socket 325 so as to be able to remove the removable rod 300 from the shaft assembly portion 200.

Referring to FIG. 2, a movable plate 835 may be present at the top 3 of the device 1. The movable plate 835 may have a first end 836, a second end 837, a top 838 and a bottom 839. The first end 836 of the movable plate 835 may face the shaft assembly portion 200 while the second end 837 of the movable plate 835 may face the back 6 of the device 1. An extended lip 840 may be present on the top 838 of the movable plate 835 at the first end 836. The extended lip 840 may allow a user to manipulate and move the movable plate 835.

The second end 837 of the movable plate 835 may have a second extended lip portion 841 (FIG. 6) which may extend outward toward the back 6 of the device 1. A claw 834 (FIG. 6) may be present on the top of the movable member 11 such that the claw 834 may grasp the second extended lip 841 of the movable plate 835 while the device 1 is being disassembled, cleaned, or the interior lumen is being visually inspected. To release the claw 843 from the second extended lip 841, the user may slightly slide the extended lip 840 forward (toward the shaft assembly portion 200). Once the claw 834 is released from the second extended lip 841 of the movable plate 835, the movable plate 835 is free and the movable member 11 may be slightly moved therein allowing the ball 305 to be inserted or removed from the ball joint assembly socket 325.

While the claw 834 is located below the movable plate 835, a spring 1400 forces the extended lip 841 of the movable plate 835 over the top of movable member 11 therein allowing the grasping mechanism 335 to be activated. Further, in this position, the movable plate 835 prevents the movable member 11 from releasing ball 305. While the claw 834 is located above the movable plate 835, the device 1 is inactive (as the ball 305 is no longer in the ball joint assembly 325) and the removable rod 300 may be unscrewed (as below) and removed from the shaft assembly portion 200 for replacement and/or cleaning, or visual inspection.

As stated above, located on the rotation knob 800 of the device 1 may be a port 410. The port 410 may be, for example, a generally cylindrical shaft extending outward from the surface of the rotation knob 800. The port 410 may have an opening 411 exposing an interior 412. A cap 413 may be temporarily inserted over the port 410 so as to prevent insufflation and smoke from escaping from the body cavity during surgery up through the shaft assembly and out into the OR. The cap 413 may be attached to the device 1 by a strap 414. A user may be able to visually inspect a small portion of the removable rod 300 through the port 410 when the cap 413 is removed from the port 410.

The interior 412 of the port 410 may extend downward to and may connect with the interior portion 202 of the shaft assembly portion 200. As a result, a fluid 175 (such as a cleaning agent or distilled water) introduced into the port 410 may pass through the port 410, through the interior portion 202 of the shaft assembly portion 200 and out through the second end 204 of the shaft assembly portion 200. While the removable rod 300 is inserted within the shaft assembly portion 200, the fluid 175 may pass through the interior portion 202 of the shaft assembly portion 200 for the primary purpose of cleaning the device.

An opening 500 may be present on the back 6 of the laparoscopic instrument 1. More specifically, the opening 500 may be present on the back of the stationary member 10 of the handle portion 2, opposite the shaft assembly portion 200 side of the handle portion housing 75. The opening 500 of the back of handle portion 2 may begin a channel 501 which may extend through the interior 155 of the handle portion 2 and through to the shaft assembly portion 200. The channel 501 may further pass through an opening channel 577 of the movable member 11. In an embodiment, to visually see through the entire device 1, the movable member 11 must be moved in the functional engaged position so that the opening channel 577 of the movable member 11 aligns with the channel 501 of the device 1. More specifically, the claw 834 must engage the second extended lip portion 841 of the movable plate 835 in order for the opening channel 577 to align with the channel 501.

The channel 501 may run along the same axis as the shaft assembly portion 200 such that when the removable rod 300 is removed from the device 1, an opening passage is created from the back of the handle portion 2, through the handle portion housing 75, and then through the entire length 600 of the shaft assembly portion 200. The opening 500 on the back 6 of the device 1 may be largely identical in size and shape as the opening 205 (FIG. 2) located at the first end 203 and the opening 206 located at the second end 204 of the shaft assembly portion 200.

While the removable rod 300 is removed from the device 1, a user may visually inspect the entire interior portion 202 of the shaft assembly portion 200 and handle portion housing 75 through the opening 500 on the back of the stationary member 10 of the device 1. Therefore, a visual inspection may be made to determine if any debris remains after the device 1 is cleaned after use.

As stated above, located within the interior of movable plate 835 may be a spring 1400. The spring 1400 may run largely parallel with respect to the shaft assembly portion 200. The spring 1400 may have a first end 530 and a second end 531. The first end 530 of the spring 1400 may be located closer to the back 6 of the device 1 and the second end 531 of the spring 1400 may be closer to the shaft assembly portion 200 of the device 1. The spring 1400 may provide resistance to the movable plate 835 by applying a force to a portion of the movable plate 835 therein forcing the movable plate 835 away from the shaft assembly portion 200. To overcome the spring 1400 force, the user forces the extended lip 840 of the movable late 835 toward the shaft assembly portion 200 of the device 1.

As stated above, the removable rod 300 may have a first end 301 and a second end 302. During use, the first end 301 of the removable rod 300 may have a ball 305 which may be temporarily secured within a ball joint assembly socket 325. The second end 302 of the removable rod 300 may be the business end of the removable rod 300 and may have, for example, a grasping mechanism 335 such as a movable jaw.

In an embodiment, the grasping mechanism 335 may have a first member 336, a second member 337 and a housing 338. The housing 338 may be generally cylindrical and may have a first end 339 and a second end 340. The first end 339 may be attached directly to the removable rod 300. The second end 340 of the housing 338 of the grasping mechanism 335 may have a threaded member 341 which may be temporarily secured into the second end 204 of the shaft assembly portion 200, which may have a corresponding groove portion for receiving the threaded member 341. During cleaning, the threaded member 341 may be unscrewed and the removable rod 300 removed from the shaft assembly portion 200.

The housing 338 may have an interior having a pivot pin 342 which may secure and allow the first member 336 and second member 337 to pivot with respect to each other. More specifically, the first member 336 and the second member 337 may move from a closed first position for grasping to an open second position for surrounding an object or body part to be grasped. The end of the first member 336 and second member 337 may have ridges 343 for better grasping an object or body part.

The pivot pin 342 may be directly secured to the removable rod 300 while the holding device 338 remains stationary at the second end 204 of the shaft assembly portion 200. As a result, as the removable rod 300 is moved slightly forward or backward (by activating the handle), the pivot pin 342 in the interior of the holding device 338 slightly moves forward or backward activating the grasping mechanism 335.

Referring now to FIGS. 2 and 6, located between the shaft assembly portion 200 and the handle portion housing 75 may be a rotation assembly 552. The rotation assembly 552 may include the rotation knob 800 and various components (as defined below) secured within an interior 553 portion of, or adjacent to, the rotation knob 800. The rotation assembly 552 may be secured to the handle portion housing 75 via a screw 924.

A first adaptor 622 may be secured within the interior 553 of the rotation knob 800. More specifically, the first adaptor 622 may be secured within the interior 553 of the rotation knob 800 near the second end 555 end of the rotation knob 800. The first adaptor 622 may be generally cylindrical having an extended cylindrical middle section 625 with a larger diameter then the ends of the first adaptor 622. The extended middle section 625 of the first adaptor 622 may have a plurality of indentations 1304 which run along the circumference of the extended middle section 625.

The first adaptor 622 may be used to snugly secure the rotation knob 800 to the handle portion housing 75 while allowing the rotation knob 800 to rotate three hundred and sixty degrees. The indentations 1304 of the first adaptor 622 may be used to receive a plurality of corresponding ball bearings 1300 (as described below). In an embodiment, a cap 621 may be secured near the first adaptor 622. The cap 621 may prevent liquid or other debris from improperly entering the second end 555 of the rotation knob 800.

A second adaptor 1000 may also be secured within the interior 553 of the rotation knob 800. The second adaptor 1000 may be located closer to the first end 554 of the rotation knob 800 than the second end 555 of the rotation knob 800. The second adaptor 1000 may have an opening 1003 which aligns with the opening 411 of the port 410 and allows the fluid 175 (such as a cleaning agent or distilled water) to be introduced into the device 1.

The second adaptor 1000 may be generally cylindrical with a shaft portion 1101 and a base portion 1100. The shaft portion 1101 may have a diameter which is less than a diameter of the base portion 1100. The base portion 1100 of the second adaptor 1000 may be located closer toward the back 6 of the device 1 than the shaft portion 1101.

A u-shaped fastener 623 may connect the first adaptor 622 to the second adaptor 1000 within the interior 553 of the rotation knob 800. The u-shaped fastener 623 may limit the distance the first adaptor 622 may move with respect to the second adaptor 1000. A spring 525 may partially surround the first adaptor 622 and may place constant pressure between the first adaptor 622 and the second adaptor 1000; forcing them slightly apart. In an embodiment, the ball bearings 1300 may be partially or completely located within the springs 525. In an embodiment, a second plurality of ball bearings 1301 may be located within the spring 525 wherein the second plurality of ball bearings 1301 is located closer to the front 5 of the device 1 than the first plurality of ball bearings 1300.

In use, when the movable handle 11 is pulled in toward the stationary member 10 the compression force inserted by the user overcomes the tension in the spring(s) 525 and 1303 and forces the first adaptor 622 and the second adaptor 1000 toward each other. As a result, the ball bearings 1300 become compressed between within the plurality of indentations 1304 of the first adaptor 622; therein preventing the rotation knob 800 from rotating. When the user releases the pressure from the movable handle 11, the pressure on the spring(s) 525 is released and the ball bearing 1300 are released from the plurality of indentations 1304 and the rotation knob 800 may rotate freely.

An O-ring 566 may be secured within the interior 553 of the rotation knob 800. The O-ring 566 may help secure the rotation knob 800 to the shaft portion assembly 200. Further, the O-ring 566 may prevent liquid or other debris from passing between the rotation knob 800 and shaft assembly portion 200.

In an embodiment, located within the handle portion housing 75, toward the front of the handle portion housing 75, may be a largely cylindrical bushing 620 which may prevent gas which is used to insuflate the patient during surgery from leaking out of the body cavity through the device 1. The bushing 620, which is lubricious, may also allow the removable rod 300 to slide smoothly through the lumen when actuated by the handle of the device 1. In an embodiment, a second bushing 1001 (this one located within the interior 553 of the rotation knob 800) may be provided which prevents insuflation and smoke from escaping from the patient's body cavity during surgery through the handle portion housing 75 into the operating room.

Although embodiments of the present invention are shown and described therein, it should be understood that various changes and modifications to the presently preferred embodiments will be apparent to those skilled in the art. Such changes and modifications may be made without departing from the spirit and scope of the present invention and without diminishing its attendant advantages. It is therefore, intended that such changes and modifications be covered by the present application.

The invention claimed is:

1. A laparoscopic surgical instrument comprising:
   a shaft having a hollow interior and having a first end and a second end;
   a housing having a first end and a second end and wherein the housing has a handle portion which operates the instrument and wherein the handle portion has a stationary member and a moveable member and wherein the second end of the housing is secured to the first end of the shaft;
   a grasping mechanism on the second end of the shaft wherein the grasping mechanism is used to grasp an object; and
   a first hollow channel running through the stationary member of the handle portion;
   a second hollow channel running through the moveable member of the handle portion;
   wherein the first hollow channel of the stationary member of the handle portion runs parallel to and along the same axis as the hollow interior of the shaft and wherein a fluid pathway extends from the first hollow channel of the stationary member through the shaft;
   a generally oval opening located on the movable member;
   a stationary pin located within the generally oval opening of the movable member wherein the stationary pin allows the movable member to move up and down with respect to the stationary member from a first position to a second position; and
   wherein the second hollow channel of the moveable member is not aligned with and not on the same axis as the first hollow channel of the stationary member in the first position and wherein the second hollow channel of the moveable member is aligned with the first hollow channel of the stationary member in the second position and wherein both the first hollow channel and second hollow channel are aligned with the hollow interior of the shaft in the second position.

2. The laparoscopic surgical instrument of claim 1 wherein the first hollow channel of the stationary member of the handle portion has a diameter substantially equal in size to a diameter of the interior of the shaft.

3. The laparoscopic surgical instrument of claim 1 further comprising:
   a locking mechanism on the housing portion wherein the locking mechanism restricts the movement of the moveable member of the handle portion and therein restricts movement of the grasping mechanism of the shaft portion.

4. The laparoscopic surgical instrument of claim 1 further comprising:
   an opening located on a first side of the housing and an opening located on the second side of the housing wherein the opening on the first side of the housing and the opening on the second side of the housing expose a ball joint assembly located within the housing and wherein a user may visually inspect the ball joint assembly through the opening on the first side or second side of the housing.

5. The laparoscopic surgical instrument of claim 4 wherein the ball joint assembly operates the grasping mechanism of the shaft.

6. The laparoscopic surgical instrument of claim 1 further comprising:
a rotating housing member located between the second end of the housing and the first end of the shaft.

7. The laparoscopic surgical instrument of claim 6 further comprising:
a liquid flush port located on the side of the rotating housing member wherein the liquid flush port has an opening allowing the flow of a liquid through the port and then through the hollow interior of the shaft.

8. The laparoscopic surgical instrument of claim 7 further comprising:
a removable cap temporarily secured over the port of the rotating housing member.

* * * * *